United States Patent [19]

Viscio et al.

[11] Patent Number: 5,723,105
[45] Date of Patent: Mar. 3, 1998

[54] VISUALLY CLEAR GEL DENTIFRICE

[75] Inventors: David B. Viscio, Monmouth Junction; Michael Collins, Hazlet; Benjamin Y. Mandanas, Freehold, all of N.J.

[73] Assignee: Colgate-Palmolive Company, New York, N.Y.

[21] Appl. No.: 713,562

[22] Filed: Sep. 13, 1996

Related U.S. Application Data

[62] Division of Ser. No. 456,351, Jun. 1, 1995, Pat. No. 5,599,526.

[51] Int. Cl.$^6$ ............... A61K 7/16; A61K 7/18
[52] U.S. Cl. .................... 424/49; 424/56
[58] Field of Search ................... 424/49–58

[56] References Cited

U.S. PATENT DOCUMENTS

| | | | |
|---|---|---|---|
| 4,894,220 | 1/1990 | Nabi et al. | 424/43 |
| 5,476,660 | 12/1995 | Somasundaran et al. | 424/49 |
| 5,514,366 | 5/1996 | Diamond | 424/49 |
| 5,531,982 | 7/1996 | Gaffar et al. | 424/49 |
| 5,599,526 | 2/1997 | Viscio et al. | 424/49 |

OTHER PUBLICATIONS

C.A. 126: 210698 of Lion JP 09012 438A2 Jan. 14, 1997.
C.A. 118: 197840 of Henkel DE 4131118A1 Mar. 25, 1993.
CA 117: 157438 of Henkel DE 4101515A1 Jul. 23, 1992.
CA 116: 66894 of Boots Gt.Br. 2242358A1 Oct. 2, 1991.
CA 126: 203596 of Lion Jpn 09012438A2 Jan. 14, 1997.
C.A. 104: 135847 of Salerno Parfums Cosmetaromes: 65.63–6, 69, 1985.
CA 102: 190829 of Gueven Parfuem. Kosmet 65(11), 705-2 (1984).
CA 77: 143745 of Unilever DE 2203379 Aug. 17, 1972.

*Primary Examiner*—Shep K. Rose
*Attorney, Agent, or Firm*—Henry S. Goldfine

[57] ABSTRACT

A visually clear gel dentifrice comprising a polishing agent having a refractive index of about 1.41 to 1.47, a substantially water-insoluble noncationic antibacterial agent, an aqueous water-humectant liquid vehicle having a refractive index with about 0.02 refractive index units of the refractive index of the polishing agent and surfactant which is a sulfated polyoxyethylene alcohol sodium or potassium salt or a weight mixture of at least 3:1 to sodium or potassium lauryl sulfate with the sulfated polyoxyethylene alcohol or a weight mixture of about 1:3 to about 3:1 of sodium potassium lauryl sulfate with an N-acyl-N-alkyl taurate sodium or potassium salt. The visually clear systems have reduced formation of surfactant crystals when subject to cool temperature.

13 Claims, No Drawings

VISUALLY CLEAR GEL DENTIFRICE

This is a division of application Ser. No. 08/456,351, filed Jun. 1, 1995, now U.S. Pat. No. 5,599,526.

BACKGROUND OF THE INVENTION

This invention relates to an antiplaque gel dentifrice which is visually clear.

Dentifrices which are visually clear are appealling to consumers. Numerous visually clear products have been sold commercially as gel dentifrices.

Clarity however, can reveal other problems. Thus, when a liquid organic gel dentifrice component acts as a solvent to facilitate dissolving of a substantially water-insoluble component, conditions can arise in which a portion of the organic solvent separates into crystals which detract aesthetically from the clear appearance of the gel dentifrice, although without negatively impacting on hygienic effectiveness.

In recent years, substantially water-insoluble non-cationic antibacterial agents have been found to be effective antiplaque agents in oral compositions, particularly when used in combination with an antibacterial-enhancing agent (AEA) which improves delivery to and retention on oral tooth and gum surfaces of the antibacterial agent. As described in U.S. Pat. Nos. 5,354,550 and 5,253,313 of Collins et al, it has been possible to prepare clear gel dentifrices containing such antibacterial agent and polycarboxylate as AEA.

The prior art considerations for attaining clarity ranging from haze or translucency to high transparency have, in general, been based upon employing a dentifrice polishing agent having a refractive index of about 1.41 to about 1.47, properly balancing with water (refractive index 1.333) and humectant, most usually glycerine (refractive index 1.473) and sorbitol (refractive index 1.457, as 70% aqueous solution). Since the refractive index of grades of siliceous polishing agents, the most frequently used type of polishing agents in gel dentifrices, is usually about 1.41 to about 1.47, although water ranges in the dentifrices such as up to about 30% by weight have been disclosed, the amount of water is generally kept low, say about 3% by weight, when transparency and not merely turbid translucency is desired.

The need to dissolve small amounts of normally insoluble materials such as noncationic antibacterial agents also can present a challenge to achieving clarity. Flavor oil and surfactant are generally used to dissolve such materials.

As indicated above, clarity can be attained in gel dentifrices containing substantially water-insoluble noncationic antibacterial agents as is described in U.S. Pat. Nos. 5,354, 550 and 5,253,213 and reasonable clarity may be obtained when polycarboxylate is present even somewhat outside of the parameters of these patents. However, when the gel dentifrice is visually clear (that is transparent or translucent) and contains a substantially water-insoluble noncationic antibacterial agent, such as triclosan, and sodium lauryl sulfate, the most common dentifrice surfactant, as an organic solvent to facilitate dissolving the antibacterial agent, under cool temperature conditions (below about 20° C.), crystals can separate from the surfactant and substantially diminish clarity of the gel dentifrice.

In the present invention, alternative surfactant systems reduced crystal formation while still permitting substantial retention of gel dentifrice clarity. These systems are particularly Tergitol® sulfate as surfactant or mixtures of sodium lauryl sulfate with Tergitol® sulfates or with taurates.

The art has previously disclosed dentifrices containing substantially water-insoluble noncationic antibacterial agent with alternative surfactant systems but without achieving the present invention. Indeed, the crystal formation problem solved in the present invention appears not to have even been recognized in the prior art.

In U.S. Pat. No. 5,135,738 to Gaffar et al, triclosan dentifrices are disclosed which may be manufactured with a mixture of sodium lauryl sulfate and sodium methyl cocoyl taurate. However, the only dentifrices which are specifically prepared which contain silica polishing agent are not clear (for instance, due to the presence of titanium dioxide, an opacifying agent.

In U.S. Pat. No. 5,356,615 to Gaffar, a mixed surfactant system of Tauranol® WS and sodium lauryl sulfate is disclosed for triclosan mouthwash. Such a system is not indicated for disclosed triclosan toothpaste with silica polishing agent, which in any event, in the manner in which it is exemplified, is not visually clear.

In Japanese Public Patent Disclosure H4-139117 to Lion Corporation a liquid dentifrice is disclosed in Example 23 which contains sodium lauryl sulfate and sodium N-lauryl-N-methyl taurate. The liquid dentifrice contains 10% zirconium silicate (which has a refractive index of about 1.9 to 2.0) and cannot be clear.

In European Patent Publication 161898 to Unilever PLC, dentifrice with silica xerogel polishing agent and triclosan is disclosed which contains sodium lauryl sulfate and sodium dodecylbenzene sulfonate. However, in clear gel dentifrices, this surfactant system would not avoid the formation of sodium lauryl sulfate crystals when the dentifrice is subject to cool temperatures.

In chapter 11 (Molecular Interactions and Synergism in Mixtures of Two Surfactants) Rosen, M. J., of "Surfactants and Interfacial Phenomena", 2nd Edition, 1989, John Wiley and Sons, Inc., New York, (pages 393–419), the author sets forth guidelines for predicting synergistic effects with particular surfactant mixtures. These guidelines, however, are applicable to water systems rather than to complete formulations such as dentifrices. Further, it is not appropriate to apply such guidelines to a problem which has not previously been recognized, such as the formation of visible sodium lauryl sulfate crystals in clear gel dentifrices subject to cool temperature conditions.

It is an advantage of this invention that stable visual clarity is attained in a gel dentifrice containing substantially water-insoluble noncationic antibacterial agent and surfactant solvent therefore, such that visible crystals are not observed as a result of surfactant separation.

Other advantages of the invention will be apparent from consideration of the following specification.

In accordance with certain of its aspects, this invention relates to a visually clear gel dentifrice comprising about 5–50% by weight of a dentally acceptable dentifrice polishing agent having a refractive index in the range of about 1.41 to about 1.47, about 0.1–10% by weight of a gelling agent to provide a gel consistency to said dentifrice, at least about 20% by weight of a liquid aqueous-humectant vehicle having a refractive index within about 0.02 refractive index units of said polishing agent, about 0.01–5% by weight of a substantially water-insoluble noncationic antibacterial agent, which is partially dissolved in about 0.1–3% by weight of flavoring oil, and about 0.5–5% by weight of surfactant which facilitates dissolving of said antibacterial agent in said gel dentifrice, the improvement characterized in that said surfactant is (a) a polyoxyethylene alcohol sulfate having the formula

wherein R is an alkyl group with a $C_{10-18}$ hydrocarbon chain length, n is an integer of 1 to about 4 and X is alkali metal or
(b) a weight mixture of at least about 1:3 of said polyoxyethylene alcohol sulfate with alkali metal lauryl sulfate or
(c) a weight mixture of about 3:1 to about 1:3 of alkali metal lauryl sulfate with an N-acyl-N-alkyltaurate having the formula:

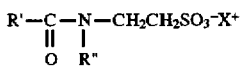

wherein R' is an alkyl group with a $C_{10-24}$ linear hydrocarbon chain length, R" is a $C_{1-4}$ n-alkyl group and X is alkali metal. As used herein, alkali metal includes the Group 1A metals, especially sodium and potassium and functionally equivalent ammonium.

Typical examples of substantially water insoluble noncationic antibacterial agents which are particularly desirable for their antiplaque effectiveness, safety and formulation are:
Halogenated Diphenyl Ethers
   2',4,4'-trichloro-2-hydroxy-diphenyl ether (Triclosan)
   2,2'-dihydroxy-5,5'-dibromo-diphenyl ether.
Halogenated Salicylanilides
   4',5-dibromosalicylanilide
   3,4',5-trichlorosalicylanilide
   3,4',5-tribromosalicylanilide
   2,3,3',5-tetrachlorosalicylanilide
   3,3,3',5-tetrachlorosalicylanilide
   3,5-dibromo-3'-trifluoromethyl salicylanilide
   5-n-octanoyl-3'-trifluoromethyl salicylanilide
   3,5-dibromo-4'-trifluoromethyl salicylanilide
   3,5-dibromo-3'-trifluoromethyl salicylanilide (Fluorophene)
Benzoic Esters
   Methyl-p-Hydroxybenzoic Ester
   Ethyl-p-Hydroxybenzoic Ester
   Propyl-p-Hydroxybenzoic Ester
   Butyl-p-Hydroxybenzoic Ester
Sesquiterpene Alcohols
   Farnesol
   Nerolidol
   Bisabolol
   Santalol
Halogenated Carbanilides
   3,4,4'-trichlorocarbanilide
   3-trifluoromethyl-4,4'-dichlorocarbanilide
   3,3,4'-trichlorocarbanilide
   Phenolic Compounds (including phenol and its homologs, mono- and poly-alkyl and aromatic halo (e.g. F, Cl, Br, I)-phenols, resorcinol and catechol and their derivatives and bisphenolic compounds). Such compounds include inter alia:
Phenol and its Homologs
   Phenol
   2-Methyl-Phenol
   3-Methyl-Phenol
   4-Methyl-Phenol
   4-Ethyl-Phenol
   2,4-Dimethyl-Phenol
   2,5-Dimethyl-Phenol
   3,4-Dimethyl-Phenol
   2,6-Dimethyl-Phenol
   4-n-Propyl-Phenol
   4-n-Butyl-Phenol
   4-n-Amyl-Phenol
   4-tert-Amyl-Phenol
   4-n-Hexyl-Phenol
   4-n-Heptyl-Phenol
   2-Methoxy-4-(2-Propenyl)-Phenol (Eugenol)
   2-Isopropyl-5-Methyl-Phenol (Thymol)
Mono- and Poly-Alkyl and Aralkyl Halophenols
   Methyl-p-Chlorophenol
   Ethyl-p-Chlorphenol
   n-Propyl-p-Chlorophenol
   n-Butyl-p-Chlorophenol
   n-Amyl-p-Chlorophenol
   sec-Amyl-p-Chlorophenol
   n-Hexyl-p-Chlorophenol
   Cyclohexyl-p-Chlorophenol
   n-Heptyl-p-Chlorophenol
   n-Octyl-p-Chlorophenol
   o-Chlorophenol
   Methyl-o-Chlorophenol
   Ethyl-o-Chlorophenol
   n-Propyl-o-Chlorophenol
   n-Butyl-o-Chlorophenol
   n-Amyl-o-Chlorophenol
   tert-Amyl-o-Chlorophenol
   n-Hexyl-o-chlorophenol
   n-Heptyl-o-Chloropenol
   p-Chlorophenol
   o-Benzyl-p-Chlorophenol
   o-Benzyl-m-methyl-p-Chlorophenol
   o-Benzyl-m, m-dimethyl-p-Chlorophenol
   o-Phenylethyl-p-Chlorophenol
   o-Phenylethyl-m-methyl-p-Chlorophenol
   3-Methyl-p-Chlorophenol
   3,5-Dimethyl-p-Chlorophenol
   6-Ethyl-3-methyl-p-Chlorophenol
   6-n-Propyl-3-methyl-p-Chlorophenol
   6-iso-propyl-3-methyl-p-Chlorophenol
   2-Ethyl-3,5-dimethyl-p-Chlorophenol
   6-sec Butyl-3-methyl-p-Chlorophenol
   2-iso-Propyl-3,5-dimethyl-p-Chlorophenol
   6-Diethylmethyl-3-methyl-p-Chlorophenol
   6-iso-Propyl-2-ethyl-3-methyl-p-Chlorophenol
   2-sec-Amyl-3,5-dimethyl-p-Chlorophenol
   2-Diethylmethyl-3,5-dimethyl-p-Chlorophenol
   6-sec-Octyl-3-methyl-p-Chlorophenol
   p-Bromophenol
   Methyl-p-Bromophenol
   Ethyl-p-Bromophenol
   n-Propyl-p-Bromophenol
   n-Butyl-p-Bromophenol
   n-Amyl-p-Bromophenol
   sec-Amyl-p-Bromophenol
   n-Hexyl-p-Bromophenol
   cyclohexyl-p-Bromophenol
   o-Bromophenol
   tert-Amyl-o-Bromophenol
   n-Hexyl-o-Bromophenol
   n-Propyl-m,m-Dimethyl-o-Bromophenol
   2-Phenyl Phenol
   4-Chloro-2-methyl phenol
   4-chloro-3-methyl phenol
   4-chloro-3,5-dimethyl phenol
   2,4-dichloro-3,5-dimethyl phenol
   3,4,5,6-tetrabromo-2-methylphenol 5-methyl-2-pentylphenol
4-isopropyl-3-methylphenol
5-chloro-2-hydroxydiphenyl-3methyl phenol Resorcinol and Its Derivatives
  Resorcinol
  Methyl-Resorcinol
  Ethyl-Resorcinol
  n-Propyl-Resorcinol
  n-Butyl-Resorcinol
  n-Amyl-Resorcinol
  n-Hexyl-Resorcinol
  n-Heptyl-Resorcinol
  n-Octyl-Resorcinol
  n-Nonyl-Resorcinol
  Phenyl-Resorcinol
  Benzyl-Resorcinol
  Phenylethyl-Resorcinol
  Phenylpropyl-Resorcinol
  p-Chlorobenzyl-Resorcinol
  5-Chloro-2,4-Dihydroxydiphenyl Methane
  4'-Chloro-2,4-Dihydroxydiphenyl Methane
  5-Bromo-2,4-Dihydroxydiphenyl Methane
  4'-Bromo-2,4-Dihydroxydiphenyl Methane Bisphenolic Compounds
  Bisphenol A (2,2-bis (4-hydroxyphenyl) propane)
  2,2'-methylene bis (4-chlorophenol)
  2,2'-methylene bis (3,4,6-trichlorophenol) (hexachlorophene)
  2,2'-methylene bis (4-chloro-6-bromophenol)
  bis (2-hydroxy-3,5-dichlorophenyl) sulfide
  bis (2-hydroxy-5-chlorobenzyl) sulfide The noncationic antibacterial agent is present in the gel dentifrice composition of the present invention in an effective antiplaque amount typically about 0.01–5% by weight, preferably about 0.03–1% and most preferably about 0.3–0.6%. The antibacterial agent is substantially water-insoluble, meaning that its solubility is less than about 1%.

The preferred halogenated diphenyl ether is triclosan. The preferred phenolic compounds are phenol, thymol, eugenol, and 2,2'methylene bis (4-chloro-6-bromophenol). The preferred sesquiterpene alcohols are nerolidol and bisabolol.

The dentally acceptable dentifrice polishing agent has a refractive index in the range of about 1.41 to about 1.47. Thus, it may be a finely divided synthetic amorphous silica having an average refractive index of from about 1.410 to 1.440 as has been described for translucent dental creams in U.S. Pat. Nos 3,939,262 and 4,007,260, each to Kim or an alkali metal phosphate salt having a refractive index between 1.435 and about 1.465 as has been described in U.S. Pat. No. 3,927,202 to Harvey et al. The alkali metal phosphate polishing agents described therein are potassium metaphosphate, which is water-insoluble and water-soluble sodium pyrophosphate dodecahydrate, dibasic sodium orthophosphate dihydrate, dibasic sodium orthophosphate heptahydrate and tribasic sodium orthophospahte dodecahydrate.

Preferably the polishing agent is a siliceous material such as a hydrous silica gel, a silica xerogel or a complex amorphous alkali metal aluminosilicate or zirconosilicate having a refractive index of about 1.44 to 1.48 or a precipitated silica having a refractive index of about 1.41 to 1.45. Colloidal silica materials include those sold under the trademark SYLOID such as those which have been sold as Syloid 72 and Syloid 74. Precipitated silicas include those sold under the trademark ZEODENT by J.M. Huber Corporation such as Zeodent 113 and Zeodent 115 and Zeodent 119.

The complex aluminosilicate salt appears to contain interbonded silica and alumina having Al-O-Si bonds as described by Tamele, "Chemical of the Surface and Activity of Alumina-Silica Craking Catalyst", Discussions of the Faraday Society, No. 8, Pages 270–279 (1950) and particularly at Page 273, FIG. 1, Curve 3 wherein the interaction between silica and aluminum ions is potentiometrically detected. Further literature describing this type of complex includes Milliken et al., "The Chemical Characteristics and Structure of Craking Catalysts", Discussions of the Faraday Society, No. 8, Pages 279–290 (1950) and particularly the sentence bridging Pages 284–285. These complexes clearly differ from silica gel as is described by Plank et al., "Differences Between Silica and Silica-Alumina Gels I. Factors Affecting the Porous Structure of These Gels," Journal of Colloid Science, 2, Pages 399–412 (1947) and Plank, "Differences Between Silica and Silica-Alumina Gels II. A Proposed Mechanism for the Gelation and Syneresis of These Gels," Journal of Colloid Science 2, Pages 423–427, (1947) in which formation of the Al-O-Si bond is described at Pages 419–422.

The liquid vehicle, when mixed with gelling agent, forms a gel mass of consistency which desirably can be extruded from a collapsible opaque or clear plastic, aluminum or lined tube or other squeeze, pump or pressurized dispenser. The liquid vehicle comprises at least about 20% by weight of the gel dentifrice (e.g. about 20–94.39%) and is typically composed of water and humectant such as glycerine, sorbitol, propylene glycol and the like. Sorbitol, glycerine and mixtures thereof are preferred humectants due to their generally excellent humectant properties and their refractive indices which permit formulation of the liquid vehicle with a refractive index within about 0.02 units of the refractive index of the polishing agent. Thus sorbitol (commercially available in 70% aqueous solution), has a refractive index of 1.457 and glycerine (99.5% aqueous solution) has a refractive index of 1.473. The refractive index of water is 1.33.

A gel vehicle containing about 25–28% water (apart from water provided as humectant solvent), about 10–12% of 99.5% glycerine solution and about 30–35% of 70% sorbitol solution can readily provide a refractive index of about 1.43 to 1.46 and permit formation of a clear gel dentifrice in which the refractive index of the polishing agent is about 1.41 to 1.47 and within 0.02 of the refractive index of the liquid vehicle.

Should the gel dentifrice contain a polycarboxylate as an antibacterial-enhancing agent (AEA) to enhance delivery and retention of the substantially water-insoluble noncationic antibacterial agent to oral tooth and gum surfaces, the relative amounts of liquid vehicle water and humectant components can be adjusted in order to provide clarity to a dentifrice containing a polishing agent having a refractive index of about 1.41 to 1.47, for instance as described in U.S. Pat. No. 5,252,313, to Collins et al, the disclosure of which is incorporated herein by reference.

When present to enhance delivery and retention of the antibacterial agent water-swellable synthetic anionic polymeric polycarboxylate typically has a molecular weight of about 1,000 to about 1,000,000 or more, preferably about 30,000 to about 500,000.

The water-swellable synthetic anionic polymeric polycarboxylates are preferably employed as partially or completely neutralized water swellable alkali metal (or ammonium) salts but may also be used in their free acids. Preferably they are 4:1 to 1:4 copolymers of maleic anhydride or maleic acid with another polymerizable ethylenically unsaturated monomer, which is very preferably methyl vinyl ether, and the copolymer will have a molecular weight in the range of about 5,000–2,000,000, preferably about 30,000–1,500,000, more preferably about 50,000–1,100,000 and most preferably about 50,000–100,000, as determined by vapor pressure osmometry. A preferred range of molecular weights, by gel permeation chromatography against a polyethylene glycol standard, is about 500,000–1,500,000, more preferably about 1,000,000–1,100,000, e.g., about 1,090,000. Useful such polycarboxylates include Luviform® FA-139 of BASF and GAF's Gantrez® AN 169, AN 139, AN 119 and S-97, pharmaceutical grade. The Gantrez polycarboxylates have been reported by their manufacturer to be of molecular weights of about 750,000, 500,000, 250,000 and 70,000, respectively, but by gel permeation chromatography determinations (against a polyethylene glycol standard) the S-97, pharmaceutical grade, is of a molecular weight in the range of about 1,000,000–1,100,000 (the lower molecular weight of 70,000, was determined by vapor pressure osmometry). The polymers such as the Luviform and Gantrez polymers may be incorporated into the gel dentifrices in solid form or in aqueous solution. When aqueous solution is employed, the aqueous solvent forms a portion of the total water in the liquid vehicle. The mentioned Luviform and Gantrez copolymers are all linear copolymers but cross-linked polymers, such as those sold under the trademark Carbopol, of BF Goodrich, e.g., Carbopol 934, 940 and 941, may be substituted, at least in part (e.g., about 1% or more). Since aqueous solutions of Gantrez copolymer are typically available as 13% solutions and aqueous solutions of Luviform copolymer can be typically available as about 25–35%, say 26% solutions, less water is introduced into the clear gel dentifrice with Luviform solution than with Gantrez solution, making it somewhat easier to maintain clarity under Luviform solution than with Gantrez solution.

Other water-swellable polymeric polycarboxylates include the 1:1 copolymers of maleic anhydride with ethyl acrylate, hydroxyethyl methacrylate, N-vinyl-2-pyrollidone, or ethylene, the later being available for example as Monsanto EMA No. 1103, M.W. 10,000 and EMA Grade 61, and 1:1 copolymers of acrylic acid with methyl or hydroxyethyl methacrylate, methyl or ethyl acrylic acid with methyl or hydroxyethyl methacrylate, methyl or ethyl acrylate, isobutyl vinyl ether or N-vinyl-2-pyrrolidone.

Additional water-swellable polymeric polycarboxylates include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable, also, generally are polymerized olefinically or ethylenically unsaturated carboxylic acid containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility, typically as alkali metal (especially sodium or potassium), including ammonium.

In addition to the described possible presence of polycarboxylates as antibacterial-enhancing agents (AEA's), other AEA's, for instance as described in U.S. Pat. No. 5,032,386 to Gaffar et al, such as polyphosphates, polyphosphinates and polysulfonate polymers may be used. The disclosure of U.S. Pat. No. 5,032,386 is incorporated herein by reference. The AEA's are non-toxic and can be present in amount of about 0.05–4% by weight, preferably about 0.1–3% more preferably about 0.5–2.5%.

Gel dentrifices have their gel consistency provided by a natural or synthetic binder, thickener or gelling agent in proportions of about 0.1 to about 10% by weight, preferably about 0.5 to about 5%.

Suitable thickeners include Irish moss, iota carrageenan, gum tragacanth starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Sodium carboxymethyl cellulose is preferred, even including grades having a viscosity above 20 cps measured as 1% aqueous solution at 25° C., e.g. CMC-7MF and CMC-7MFX available from Hercules.

It will be understood that, as is conventional, the gel dentifrice preparations are to be sold or otherwise distributed in suitably labeled collapsible tubes, typically aluminum, lined lead or opaque or clear plastic, or other squeeze, pump or pressurized dispenser for metering out the contents, having a label describing it in substance, as a gel dentifrice or toothpaste.

Organic surface-active agents are used in the compositions of the present invention to achieve increased prophylactic action, assist in achieving thorough and complete dispersion of the dentifrice throughout the oral cavity, and render the instant compositions more cosmetically acceptable. The particular organic surfactant employed in the present invention is anionic and is present in amount of about 0.5–5% by weight, preferably about 0.8–3.5%. While it imparts to the composition detersive and foaming properties, it also exercises solvent properties for the substantially water-insoluble non-cationic antibacterial agent and provides visually clear gel dentifrices containing such antibacterial agents with reduced tendency to form unsightly crystals when the gel dentifrice is subject to cool temperatures, below about 20° C., such as between about 5° to 15° C.

The surfactant may desirably be the anionic sulfate of the nonionic polyoxyoxyeghylenated alcohol available under the name Tergitol® from Union Carbide Company. A preferred sulfate Terigol, available as Terigol 24,L-2NMW Sulfate, is represented by the formula:

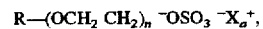

wherein X is Na, n is an average of 2 and R has a linear hydrocarbon length is 12–14. However, more generally X is alkali metal such as sodium or potassium (and including functionally equivalent ammonium), n is an integer of 1 to about 4, preferably 2, and R is an alkyl group with linear hydrocarbon chain length of $C_{10-18}$, preferably $C_{12-16}$.

The sulfated surfactant having the general formula represented above can be used in amount of about 0.5–5% by weight, preferably about 0.8–2.5%, most preferably about 1.2–2.5%, as the sole surfactant or in at least about 1:3 mixture with alkali metal lauryl sulfate alcohol sulfate salt, typically about 1:3 to about 3:1 and preferably about 1:1 to about 1:3 of the sulfated polyoxyethylenated alcohol to the lauryl sulfate.

The surfactant may also be a mixture of an N-acyl N-alkyltaurate alkali metal salt with alkali metal lauryl sulfate, in a weight ratio of the taurate to the lauryl sulfate of about 3:1 to about 1:3, preferably about 1:1 to about 1:3, most preferably about 1:1.

A preferred taurate is available from Finetex Inc. as Tauranol® WHSP, represented by the formula:

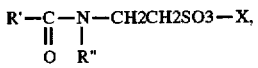

wherein R' is cocoyl, R" is methyl and X is sodium. However, more generally, X can be alkali metal such as sodium or potassium (and including functionally equivalent ammonium), R' is an alkyl group with $C_{10-18}$ linear hydrocarbon chain length, preferably $C_{12-16}$ and R" is a $C_{1-4}$ n-alkyl group, preferably methyl.

Representive taurates include the sodium and potassium salts of N-cocoyl-N-methyltaurate, N-palmitoyl-N-methyltaurate and N-oleyl-N-methyl taurate and their ethyl, n-propyl and n-butyl homologs.

When the surfactant is a mixture of the described salts it is preferred that when one is sodium salt that the other is also; or that each be potassium salts or ammonium salts. Sodium salts are preferred.

Various other materials may be incorporated in the gel dentifrices of this invention such as preservatives, silicones, anticalculus agents, water-soluble dyes, iridescent particles and/or ammoniated material such as urea, diammonium phosphate, and mixtures thereof. These adjuvants, where present, are incorporated in the preparations in amounts which do not substantially adversely affect the properties and characteristics desired.

Any suitable flavoring oil or sweetening material may also be employed. Flavoring oil partially dissolves the noncationic antibacterial agent. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, d-tryptophan, dihydrochalcones, sodium cyclamate, perillartine, APM (aspartyl phenyl alanine, methyl ester), saccharine and the like. Suitably, flavor and sweetening agents may together comprise from about 0.1% to 5% by weight or more of the preparation, with flavoring oil typically being up to about 3% and sweetening agent typically up to about 2%.

The visually clear gel dentifrices may be prepared in accordance with generally employed preparation techniques, with uniform appearance or with stripes, at least one of which is visually clear. They typically have a pH of about 4.5 to 9, generally about 5.5 to 8, preferably about 6 to 8.

The following examples are further illustrative of the nature of the present invention, but it is understood that the invention is not limited thereto. All amounts and proportions referred to herein and in the appended claims are by weight unless otherwise indicated. In the formulations of the examples various ingredients are introduced in aqueous solutions, such as 70% sorbitol and 26% Luviform F-139, in accordance with commercial practice. However, the parts set forth for all ingredients are in a non-aqueous active ingredient basis, with the exception of water.

EXAMPLE 1

The following visually clear gel dentifrices are prepared and stored at 20° C., 15° C., 10° C. and 5° C. for 1 hour.

| Ingredients | A (All SLS) Parts | B (SLS/ Tauranol) Parts | C (SLS/ Tauranol) Parts |
|---|---|---|---|
| Glycerin | 11.540 | 11.540 | 11.540 |
| Sorbitol | 33.117 | 33.117 | 33.117 |
| Water | 26.398 | 25.898 | 26.898 |
| Sodium Carboxymethyl Cellulose 12M8P | 1.000 | 1.000 | 1.000 |
| Sodium fluoride | 0.243 | 0.243 | 0.243 |
| Sodium saccharin | 0.300 | 0.300 | 0.300 |
| Luviform F-139 | 2.000 | 2.000 | 2.000 |
| Sodium hydroxide | 0.600 | 0.600 | 0.600 |
| Blue dye #1 | 0.002 | 0.002 | 0.002 |
| Zeodent Precipitated Silica polishing agent (Refractive Index: 1.440) | 18.000 | 18.000 | 18.000 |
| Sident 22S-Silica thickener | 3.500 | 3.500 | 3.500 |
| Flavor | 1.000 | 1.000 | 1.000 |
| Propylene glycol | 0.500 | 0.500 | — |
| Triclosan | 0.300 | 0.300 | 0.300 |
| Sodium lauryl sulfate | 1.500 | 1.000 | 0.750 |
| Tauranol WHSP | — | 1.000 | 0.750 |

Each of visually clear dentifrices A, B and C are extruded in ribbons having a thickness of 5 mm and the relative light transparencies of each is compared using a Gossen N-100 photograph light meter and a scale of 0.0 to 1.0 was determined after cooling to particular temperatures for 1 hour.

Gel dentifrice A, with 1.5 parts of sodium lauryl sulfate (SLS) as the only surfactant, reveals a relative light transmission of about 1.0 at 20° C. and 15° C. and of 0.75 at 10° C. but is very cloudy with a relative light transmission of about 0.1 at 5° C., due to substantial formation of SLS crystals at the low temperature.

On the other hand gel, following similar extrusion, Dentifrice B, with 2.0 parts of mixed 1:1 SLS:Tauranol surfactant reveals a relative light transmission of about 1.0 at 20° C. and 15° C. and of about 0.95 at 10° C. and 5° C., thereby indicating very little SLS crystal separation and substantial solution of the antibacterial agent, while the temperature is reduced.

Gel dentifrice C, with 1.5 parts of mixed 1:1 SLS:Tauranol surfactant, following similar extrusion, reveals a relative light transmission of about 0.625 at 20° C., and of about 0.59, 0.59 and 0.6, thus indicating somewhat less solution of antibacterial agent than gel dentifrices A and B, but still substantial visual clarity while there is substantially no SLS crystal separation as the temperature is reduced.

In the dentifrices above similar effects are obtained when 0.76 parts of sodium monofluorophosphate replace 0.243 parts of sodium fluoride with appropriate adjustment of amounts of sorbitol to provide 100.000 parts of dentifrice.

When gel dentifrices B and C are modified with sodium dodecylbenzene sulfonated (DDBS) replacing Tauranol to provide 1:1 mixtures of SLS with DDBS, substantial SLS crystal formation occurs when the gel dentifrices are cooled below 20° C.

EXAMPLE 2

Compositions are prepared similar to those of Example 1 except that silica material (18 parts Zeodent 113 and 3.5 parts Sident 22S) is omitted. These compositions are gel phase formulas for dentifrice gels in which the refractive index of the liquid vehicle (water-humectant) corresponds closely (within 0.02 units) to the refractive index of the omitted silica material.

The gel phase formulas are:

| | D Parts | E Parts | F Parts | G Parts | H Parts | I Parts |
|---|---|---|---|---|---|---|
| Glycerin | 14.738 | 14.645 | 14.645 | 14.645 | 14.645 | 14.645 |
| Sorbitol | 42.295 | 42.027 | 42.027 | 42.027 | 42.027 | 42.027 |
| Water | 33.462 | 33.249 | 33.249 | 33.249 | 33.249 | 33.249 |
| CMC | 1.277 | 1.269 | 1.269 | 1.269 | 1.269 | 1.269 |
| Sodium fluoride | 0.310 | 0.308 | 0.308 | 0.308 | 0.308 | 0.308 |
| Sodium saccharin | 0.383 | 0.381 | 0.381 | 0.381 | 0.381 | 0.381 |
| Luviform F-139 | 2.554 | 2.538 | 2.538 | 2.538 | 2.538 | 2.538 |
| Sodium hydroxide | 0.766 | 0.761 | 0.761 | 0.761 | 0.761 | 0.761 |
| Flavor | 1.277 | 1.269 | 1.269 | 1.269 | 1.269 | 1.269 |
| Propylene glycol | 0.639 | 0.634 | 0.634 | 0.634 | 0.634 | 0.634 |
| Triclosan | 0.383 | 0.381 | 0.381 | 0.381 | 0.381 | 0.381 |
| Sodium lauryl sulfate | 1.916 | 2.538 | 1.904 | 1.269 | 0.634 | — |
| Tauranol WHSP | — | — | 0.634 | 1.269 | 1.904 | 2.538 |

Samples of each gel phase composition are observed at 20° C. and upon extension in a ribbon 5 mm thick after cooling for 1 hour to each of 15° C., 10° C. and 5° C.

| | | Observations | |
|---|---|---|---|
| 20° C. | 15° C. | 10° C. | 5° C. |
| | | D-All SLS | |
| Cloudy* | Opaque (SLS Crystals) | Opaque (SLS crystals) | Opaque (SLS crystals) |

*At 20° C. low dissolution of triclosan in flavor oil is observed prior to addition of SLS.

| | | E-All SLS | |
|---|---|---|---|
| Clear | Opaque (SLS Crystals) | Opaque (SLS crystals) | Opaque (SLS crystals) |
| | | F-1:3 Tauranol:SLS | |
| Clear | Clear | Slightly cloudy | Opaque |
| | | G-1:1 Tauranol:SLS | |
| Clear | Clear | Clear | Very slightly cloudy |
| | | H-3:1 Tauranol:SLS | |
| Cloudy* | Cloudy | Cloudy* | Cloudy* |

*At 20° C. low dissolution of triclosan in flavor oil is observed prior to addition of SLS, an effect still observable at 15° C., 10° C. and °C.

| | | I-All Tauranol | |
|---|---|---|---|
| Opaque* | | | |

*Tauranol is not completely dissolved in the gel phase.

From these observations it is seen that clarity is poor due to SLS crystal formation upon cooling of all SLS formulas (D and E) and is poor even at room temperature due to Tauranol insolubility in the all Tauranol formula (I).

Substantial clarity or cloudiness (but not opacity) is retained at 15° C. and 10° C. with 1:3, 1:1 and 3:1 Tauranol:SLS formulas (F, G and H) and at 5° C. with 1:1 and 3:1 Tauranol:SLS. No SLS crystals are seen in the clear, slightly cloudy and very slightly cloudy observations of the formulas with Tauranol/SLS mixtures.

EXAMPLE 3

Gel phase compositions similar to those of Example 2 are prepared except that the mixed surfactant formulas contain sulfated Tergitol surfactant in place of Tauranol. The compositions are placed in dentifrice tubes.

The gel phase formulas are:

| | J Parts | K Parts | L Parts | M Parts |
|---|---|---|---|---|
| Glycerin | 14.645 | 14.645 | 14.645 | 14.645 |
| Sorbitol | 42.027 | 42.027 | 42.027 | 42.027 |
| Water | 33.249 | 33.249 | 33.249 | 33.249 |
| CMC | 1.269 | 1.269 | 1.269 | 1.269 |
| Sodium fluoride | 0.308 | 0.308 | 0.308 | 0.308 |
| Sodium saccharin | 0.381 | 0.381 | 0.381 | 0.381 |
| Luviform F-139 | 2.538 | 2.538 | 2.538 | 2.538 |
| Sodium hydroxide | 0.761 | 0.761 | 0.761 | 0.761 |
| Flavor | 1.269 | 1.269 | 1.269 | 1.269 |
| Propylene glycol | 0.634 | 0.634 | 0.634 | 0.634 |
| Triclosan | 0.381 | 0.381 | 0.381 | 0.381 |
| Sodium lauryl sulfate | 1.904 | 1.269 | 0.634 | — |
| Sulfated Tergitol 24-L2NMW | 0.634 | 1.269 | 1.904 | 2.538 |

Samples of each gel phase composition are observed after extrusion from the tubes in ribbons of 5 mm thickness at 20° C. and after cooling for 1 hour to 15° C., 10° C. and 5° C. upon extrusion in a ribbon 5 mm thick.

| | | Observations | |
|---|---|---|---|
| 20° C. | 15° C. | 10° C. | 5° C. |
| | J-1:3 Sulfated Tergitol:SLS | | |
| Clear | Clear | Opaque | Opaque |
| | K-1:1 Sulfated Tergitol:SLS | | |
| Translucent | Translucent* | Translucent** | Opaque |

*At 15° C. a moderate schlieren effect is observed. Schlieren is a photographic technique in which density gradients in a volume of flow are made visible in a picture or image produced by refraction and light scattering from regions of changing refractive index. In the context of the present observations it is indicative degrees of separation between liquid components.
**At 10° C. a substantial schlieren effect is observed.

| | L-3:1 Sulfated Tergitol:SLS | | |
|---|---|---|---|
| Translucent* | Translucent* | Translucent* | Translucent* |

*A mild schlieren effect is observed.

| | M-All Sulfated Tergitol | | |
|---|---|---|---|
| Translucent* | Translucent* | Translucent* | Translucent* |

*A mild schlieren effect is observed.

The observations of SLS crystal formation upon cooling of all SLS formulas D and E are described in Example 2, above.

Substantial clarity, including translucency, is retained with formulas J, K, L and M, (1:3, 1:1 and 3:1 Sulfated Tergitol:SLS and all sulfated Tergitol) at 15° C. At 10° C. substantial clarity is retained with the 1:1 and 3:1 mixtures (K and L) and all sulfated Tergitol. At 5° C. substantial clarity is retained with the 3:1 mixture and all sulfated Tergitol (L and M). No SLS crystals are seen in the formulas which contain mixtures of sulfate Tergitol with SLS (J, K and L) in the clear and translucent observations nor are any crystals seen in the observations of the Sulfated Tergitol formula (M).

This invention has been described with respect to certain preferred embodiments and it will be understood that modifications and variations thereof obvious to those skilled in the art are to be included within the purview of this application and the scope of the appended claims.

We claim:

1. A visually clear gel dentifrice comprising about 5–50% by weight of dentally acceptable dentifrice polishing agent having a refractive index in the range of about 1.41 to about 1.47, about 0.1–10% by weight of a gelling agent to provide a gel consistency to said dentifrice, at least about 20% by weight of a liquid aqueous-humectant vehicle having a refractive index within about 0.02 refractive index units of said polishing agent, about 0.01–5% by weight of a substantially water-insoluble noncationic antibacterial agent, which is partially dissolved in about 0.1–3% by weight of flavoring oil, and about 0.5–5% by weight of surfactant which facilitates dissolving of said antibacterial agent in said gel dentifrice, the improvement characterized in that said surfactant is (a) a polyoxyethylene alcohol sulfate having the formula $$R\text{—}(O\ CH_2\ CH_2)_n\text{—}OSO_3{}^-X^+,$$

wherein R is an alkyl group with a C10–18 hydrocarbon chain length, n is an integer of 1 to about 4 and X is alkali metal or (b) a weight mixture of at least about 1:3 of said polyoxyethylene alcohol sulfate with alkali metal lauryl sulfate;

wherein formations of crystals at cool temperature conditions below about 20° C. which substantially diminish clarity of said clear gel dentifrice is reduced while still permitting substantial retention of gel dentifrice clarity.

2. The visually clear dentifrice claimed in claim 1 wherein said polyoxyethylene alcohol sulfate is present.

3. The visually clear dentifrice claimed in claim 2 wherein n in said polyoxyethylene alcohol sulfate is 2.

4. The visually clear dentifrice claimed in claim 3 wherein R in said polyoxyethylene alcohol is $C_{12-16}$.

5. The visually clear dentifrice claimed in claim 1 wherein said mixture of polyoxyethylene alcohol sulfate with alkali metal lauryl sulfate is present.

6. The visually clear dentifrice claimed in claim 5 wherein n in said polyoxyethylene alcohol sulfate is 2.

7. The visually clear dentifrice claimed in claim 6 wherein R in said polyoxyethylene alcohol is $C_{12-16}$.

8. The visually clear dentifrice claimed in claim 1 wherein said antibacterial agent is selected from the group consisting of halogenated diphenyl ethers, halogenated salicylanilides, benzoic esters, sesquiterpene alcohols, halogenated carbanilides and phenolic compounds.

9. The visually clear dentifrice claimed in claim 8 wherein said antibacterial agent is a halogenated diphenyl ether.

10. The visually clear dentifrice claimed in claim 9 wherein said halogenated diphenyl ether is 2',4,4'-trichloro-2-hydroxy-diphenyl ether.

11. The visually clear dentifrice claimed in claim 1 wherein said dentifrice contains a polycarboxylate antibacterial enhancing agent which enhances delivery and retention of said antibacterial agent to oral tooth and gum surfaces.

12. The visually clear dentifrice claimed in claim 11 wherein said polycarboxylate antibacterial enhancing agent is a 4:1 to 1:4 copolymer of maleic anhydride or maleic acid with another polymerizable ethylenically unsaturated monomer.

13. The visually clear dentifrice claimed in claim 12 wherein said polymerizable ethylenically unsaturated monomer is methyl vinyl ether.

* * * * *